(12) United States Patent
Strandberg

(10) Patent No.: US 7,212,863 B2
(45) Date of Patent: May 1, 2007

(54) IMPLANTABLE MEDICAL DEVICE OPERABLE IN A SPECIAL MODE UPON ACTIVATION DURING A PROGRAMMED TIME

(75) Inventor: Hans Strandberg, Sundbyberg (SE)

(73) Assignee: St. Jude Medical AB, Jarfalla (SE)

( * ) Notice: Subject to any disclaimer, the term of this patent is extended or adjusted under 35 U.S.C. 154(b) by 107 days.

(21) Appl. No.: 10/528,671

(22) PCT Filed: Jun. 23, 2003

(86) PCT No.: PCT/SE03/01082
§ 371 (c)(1),
(2), (4) Date: Mar. 22, 2005

(87) PCT Pub. No.: WO2004/026395
PCT Pub. Date: Apr. 1, 2004

(65) Prior Publication Data
US 2006/0074455 A1    Apr. 6, 2006

(30) Foreign Application Priority Data
Sep. 23, 2002    (SE) .................................... 0202803

(51) Int. Cl.
*A61N 1/00*    (2006.01)
(52) U.S. Cl. ........................... 607/30; 607/27; 607/59; 607/16; 607/32
(58) Field of Classification Search ................... 607/16, 607/27, 30, 32, 59
See application file for complete search history.

(56) References Cited

U.S. PATENT DOCUMENTS

| 4,390,020 | A | | 6/1983 | Herpers |
| 4,875,483 | A | | 10/1989 | Vollmann et al. |
| 4,944,298 | A | * | 7/1990 | Sholder ....................... 607/14 |
| 5,292,342 | A | | 3/1994 | Nelson et al. |
| 5,722,998 | A | | 3/1998 | Prutchi et al. |
| 6,216,038 | B1 | | 4/2001 | Hartlaub et al. |
| 6,370,432 | B1 | * | 4/2002 | Conley et al. ................ 607/27 |
| 6,424,867 | B1 | | 7/2002 | Snell et al. |

* cited by examiner

*Primary Examiner*—Robert E. Pezzuto
*Assistant Examiner*—Natasha Patel
(74) *Attorney, Agent, or Firm*—Schiff Hardin LLP

(57) ABSTRACT

An implantable medical device is operable in a normal mode of operation, including a test mode, as well as in at least one other mode of operation outside of the normal mode. The device has a signal detector that is responsive to an external activation and a timer that can be programmed with a specified time period. If the external activation is detected by the signal detector during the programmed time period, the medical device is operated in a mode outside of the normal mode. The medical device enters into the test mode, within the normal mode, if the external activation is detected by the signal detector outside of the time period.

15 Claims, 3 Drawing Sheets

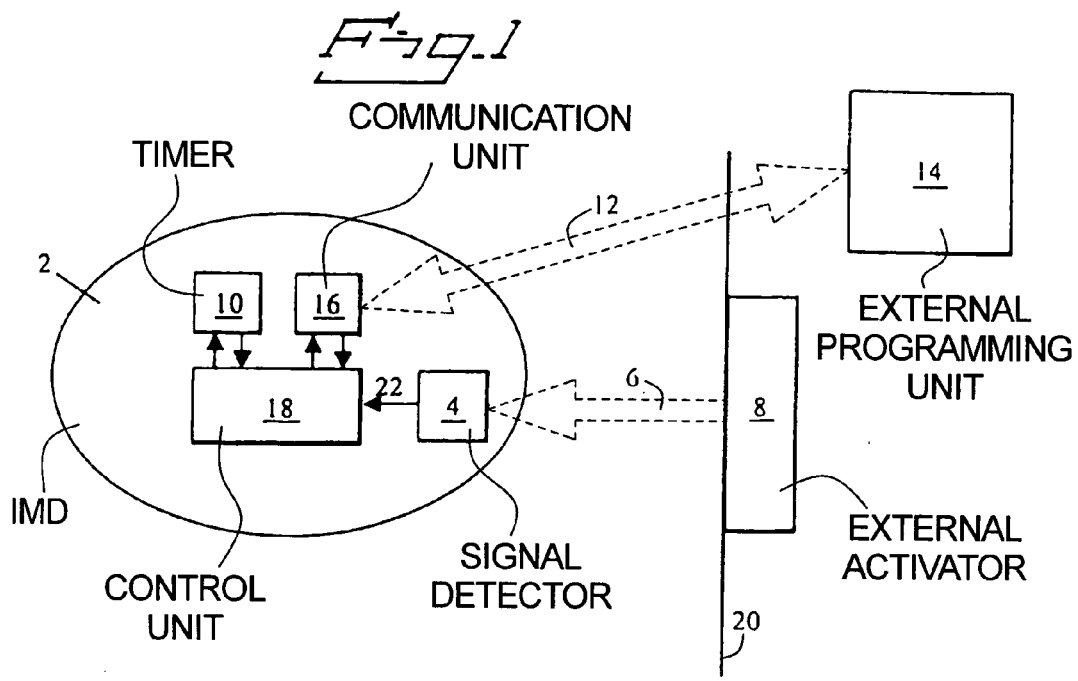
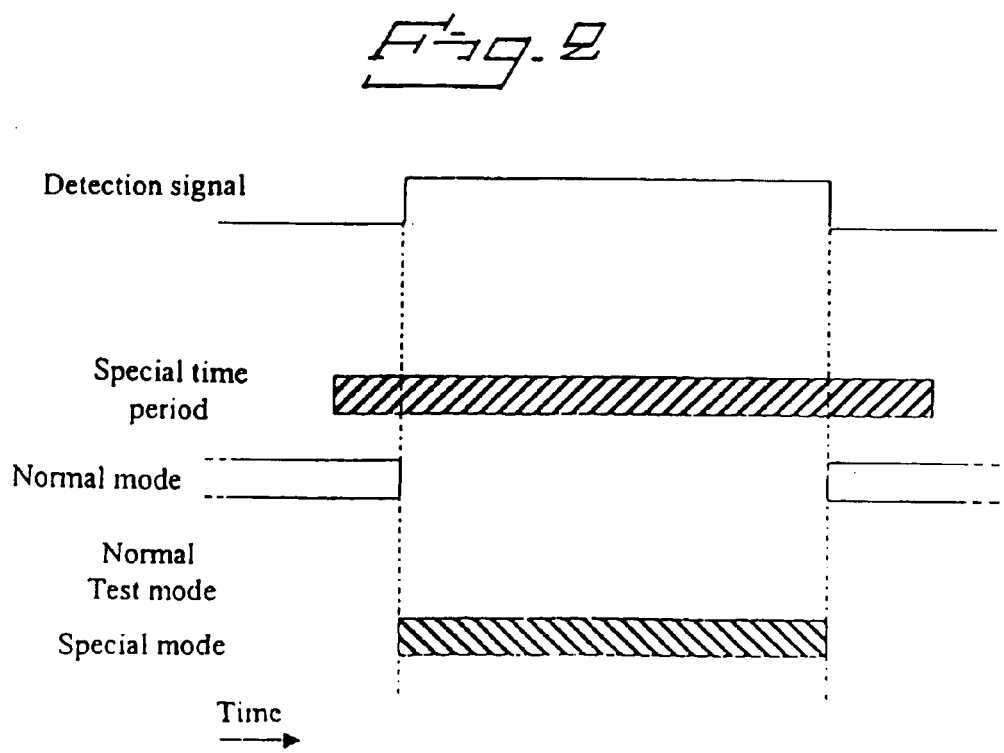

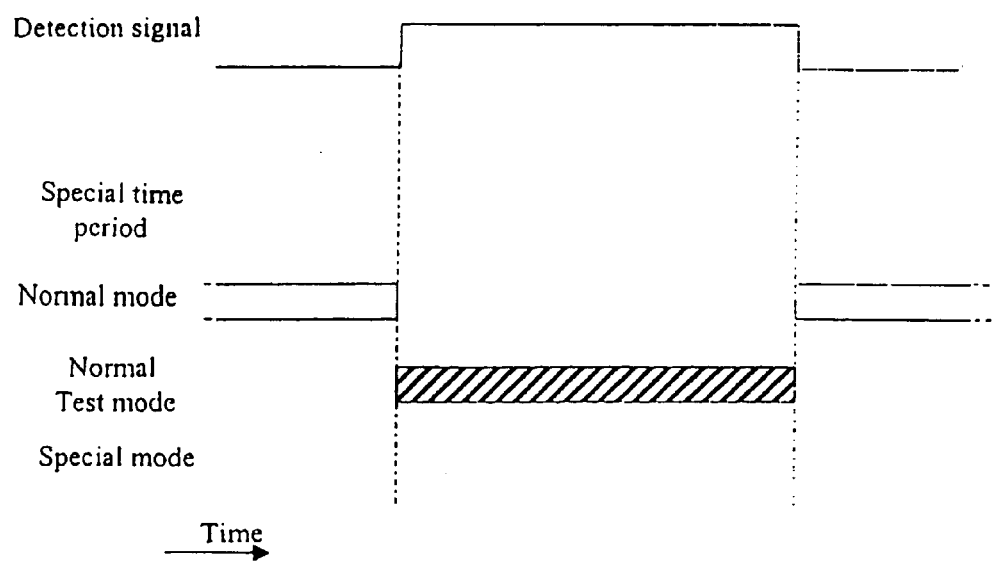
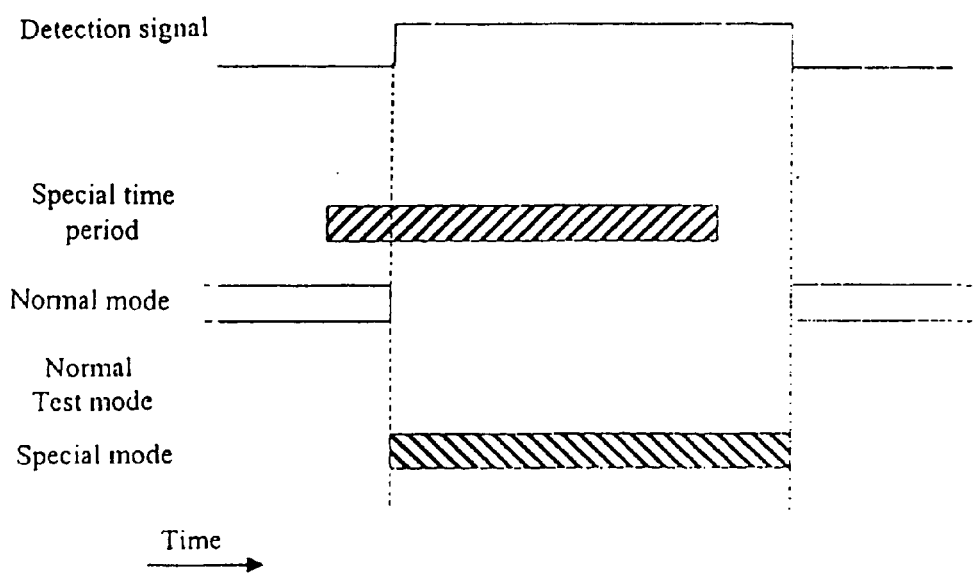

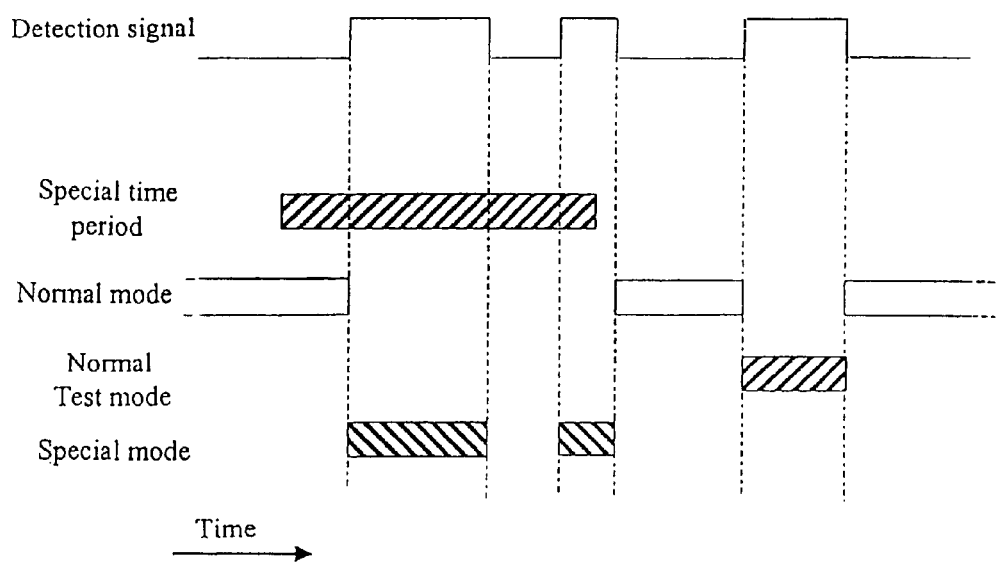

IMPLANTABLE MEDICAL DEVICE OPERABLE IN A SPECIAL MODE UPON ACTIVATION DURING A PROGRAMMED TIME

BACKGROUND OF THE INVENTION

1. Field of the Invention

The present invention relates to an implantable medical device according to the preamble of the independent claim.

2. Description of the Prior Art

It is known in the field of implantable heart stimulators or pulse generators to use a magnet to change the pacemaker to a predetermined test mode, for indication of e.g. battery condition. Other predetermined modes may for instance be threshold tests or diagnostic data storage etc. When such a test is performed a magnetically strong test magnet is held at the skin of the patient in order to activate a detector. An activation of the detector results in a "magnet ON" detection, which in turn results in a change to the predetermined mode. Such a pacemaker is for instance disclosed in U.S. Pat. No. 4,390,020.

U.S. Pat. No. 5,722,998 discloses an implantable medical device including a GMR sensor that inter alia is used to detect the presence of a magnetic field from a permanent magnet. When a magnetic field is detected the sensor causes the operation of the implantable device to revert to a magnet mode (also referred to as safe mode) of operation in which a predetermined, typically asynchronous, ventricular pacing rate is emitted.

However, some medical interventions might interfere with the function of an implantable pulse generator such as a pacemaker. Examples are electrosurgery, diathermal treatment etc. In these cases one possibility is to program the IPG into a safe mode during the entire intervention. The device according to the '998 patent of course allows this, but at the cost of not allowing the device to be provided with a magnet test mode, since the magnet mode is reserved for the safe mode. The device according to the '020 patent does not allow a safe mode, but does allow the magnet test mode. To obtain a safe mode the device according to the '020 patent the device would have to be extensively reprogrammed by a cardiologist both before and after the medical intervention.

SUMMARY OF THE INVENTION

An object of the present invention is to provide an IPG that is more flexible in regard of the magnet mode than the prior art discussed above. It should be noted that, although the above prior art description is based on magnetic signal detectors, the advantages achieved by the invention encompass other signal detectors allowing a simple yes/no or on/off response to a signal.

The above object is achieved in an implantable medical device according to the invention having a mode control that operates components of the implantable medical device in a normal mode that includes a test mode, as well in at least one other mode that is outside of said normal mode. The implantable medical device has a signal detector that is responsive to an external activation and a timer that can be programmed with a specified time period. The signal detector and the timer are connected to the mode control, and if the external activation occurs during the time period, the mode control operates the components in the mode of operation that is outside of the normal mode, and if the signal detector detects the external activation outside of the time period, the mode control operates the components in the test mode within the normal mode.

The present invention offers the opportunity to customize the behavior of an implantable medical device during a defined time period.

The new usage of applying the test magnet is that the magnet response is not the normal specified test behavior during a specific period. The function during magnet application will instead be what specifically has been ordered. The specific period has a limited length that is determined during a programming session. After that specific period has passed, the normal test behavior will occur upon magnet application, It is known in the prior art that a device, e.g. an implantable pacemaker, may have different programmed magnet responses, but the feature that after a predefined, limited tune period the specific behavior will end and the device will revert to the normal magnet response behavior is not known in the prior art.

DESCRIPTION OF THE DRAWINGS

FIG. 1 is a schematic block diagram of the present invention.

FIGS. 2–5 show time diagrams of three different scenarios that illustrate different aspects of the present invention.

DESCRIPTION OF THE PREFERRED EMBODIMENTS

FIG. 1 is a schematic block diagram of the present invention including an implantable medical device 2 adapted to be operated in a normal mode of operation and in at least one other mode of operation and provided with a signal detector 4 responsive of an external activation 6 from an external activation means 8. The signal detector 4 is preferably a magnetic sensor responsive of an externally generated magnetic field. The magnetic sensor may be e.g. a reed element, a GNIR sensor or a Hall sensor.

The medical device is provided with a special timer 10 adapted to be programmed with a specified time period (as indicated with the arrow 12). The programming is performed by an external programming unit 14 outside the body that communicates, e.g. via radio signals, with a communication unit 16 in the medical device.

The medical device further includes a control unit 18 responsive for the overall control of the function of the medical device. The different parts of the medical device are energized by a battery means (not shown).

According to a preferred embodiment of the present invention the medical device is an implantable heart stimulator, e.g. a pacemaker, a cardioverter or a defibrillator. In this case the medical device also includes a therapy means (not shown) adapted to generate a specific therapy.

The medical device is adapted to enter a predefined special mode of operation if an external activation is detected by the signal detector 4 during the specified time period, and the device is adapted to enter a normal test mode of operation if an external activation is detected by the signal detector 4 outside the specified time period.

In the preferred embodiment where the medical device is a pacemaker a normal mode of operation may be a DDD mode, i.e. a dual chamber pacemaker provided with pacing and sensing capabilities in both heart chambers and having an inhibiting and triggering response to sensing.

If an external activation element 8, preferably a magnet is held at the skin 20 close to the medical device the mode of operation may be changed to a normal test mode.

As indicated above the normal test mode may be for example for indication of the battery condition, for initiating a test of the stimulation threshold or to start ECG recordings or other diagnostic data storage.

The predefined special mode of operation is a safe operating mode where typically an asynchronous, ventricular pacing rate is issued. The parameters used to define the safe operating mode and the specified time period are preferably programmed and communicated to the communication means during one and the same programming session before a medical intervention.

The specified time period may in principle have any feasible value, but a practical upper limit may be a week and a lower limit may be in the order of a few hours, e.g. 1 hour.

FIGS. 2–5 show time diagrams of three different scenarios that illustrate different aspects of the present invention.

Each of the FIGS. 2–5 shows, from above, the detection signal in the normal state (low) or in the detection state (high), and below follows horizontal bars representing the special time period, the normal mode of operation, the normal test mode of operation and the special mode of operation.

The signal detector 4 is adapted to generate a detection signal 22 (see FIG. 1) that is set in a detection state upon the detection of an external activation and remains in the detection state as long as the external activation persists. The detection signal is normally in a normal state.

The specified time period is normally much longer than the duration for the external activation.

In FIG. 2 the present invention is illustrated.

In a typical situation where the present invention is applicable the patient is scheduled for e.g. a surgical operation involving some kind of procedure that could affect the functioning of the patient's pacemaker. The patient first visits his or her cardiologist, e.g. the same day as the operation or some day before, who determines proper safe parameter settings, this being the special mode of operation, for the pacemaker during the surgical operation and also determines the special time period this setting should be used when an external activation is detected by the signal detector 4. The cardiologist then programs the pacemaker with the determined parameter settings and the special time period using the external programming means.

The special time period preferably starts to run immediately after the special timer 10 is programmed but could alternatively start to run a predetermined time after the programming is performed. This alternative situation could happen if the patient visits the cardiologist on a Friday and the planned surgical operation is during the next week (Monday to Friday).

The patient then can undergo the planned surgical operation without the presence of the cardiologist. During the critical part(s) of the operation the surgeon/physician places a magnet on the skin outside the pacemaker that causes the pacemaker to enter the safe special mode of operation and to remain in that mode as long as the magnetic field is detected by the signal detector 4. This is seen in FIG. 2 as the horizontal bar representing the special mode that is activated when the detection signal is in its detection state.

When the magnet is taken away the pacemaker returns to the normal mode of operation. In FIG. 2 the duration of the detection signal in the detection state is, for illustrative purposes, much longer compared to the duration of the special time period than in most actual situations when the invention is used.

FIG. 3 illustrates the behavior of the medical device if no special time period has been programmed, i.e. the normal test mode is activated when an external activation (the detection signal in a detection state) is applied.

FIG. 4 illustrates the unusual situation that occurs if the special time period runs out before the external activation is terminated. In that case the medical device remains in the special mode of operation entered during the specified time period even if the specified time period times out, as long as the detection signal is in the detection state.

FIG. 5 illustrates a combination of the different scenarios shown in FIGS. 2–4 where a number of (three) activations are made, two within the duration of the special time period and one outside.

According to an alternative embodiment of the present invention the external activation are radio signals generated by the external activation means that may be included in the external programming unit. The radio signals being the external activation then includes a signaling message in the form of e.g. radio pulses coded to be interpreted as activation, i.e. the detection signal is set in a detection state.

In this alternative embodiment the special mode of operation is ended by an external deactivation including a signaling message in the form of e.g. radio pulses coded to mean deactivation.

According to another alternative embodiment the external activation has the form of light signals, either as continuous light or as activation and deactivation light pulses. The signal detector 4 is in this embodiment any suitable optical sensor.

Although modifications and changes may be suggested by those skilled in the art, it is the invention of the inventor to embody within the patent warranted heron all changes and modifications as reasonably and properly come within the scope of his contribution to the art.

I claim as my invention:

1. An implantable medical device comprising:
   a mode control that operates device components in a normal mode, including a test mode, and in at least one other mode outside of said normal mode;
   a signal detector, responsive to an external activation, connected to said mode control;
   a programmable timer connected to said mode control, said programmable timer being programmable to set a specified time period; and
   said mode control operating said device components in said other mode of operation outside of said normal mode if said external activation is detected by said signal detector during said time period, and causing said device components to operate in said test mode, within said normal mode, if said external activation is detected by said signal detector outside of said time period.

2. An implantable medical device as claimed in claim 1 wherein said mode control is programmable, simultaneously with programming of said timer, to operate said device components in a safe operating mode as said other mode of operation outside of said normal mode.

3. An implantable medical device as claimed in claim 1 wherein said timer is programmable to set said time period to be less than five days.

4. An implantable medical device as claimed in claim 1 wherein said timer is programmable to set said time period to be less than five hours.

5. An implantable medical device as claimed in claim 1 wherein said signal detector emits a detection signal in a detection state upon detection of said external activation.

6. An implantable medical device as claimed in claim 5 wherein said signal detector continues to emit said detection signal in said detection state as long as said external activation persists.

7. An implantable medical device as claimed in claim 6 wherein said mode control maintains said device components in said other mode of operation outside of said normal mode if said time period expires but said detection signal is in said detection state.

8. An implantable medical device as claimed in claim 1 wherein said timer begins said time period simultaneously with programming of said timer.

9. An implantable medical device as claimed in claim 1 wherein said timer begins said time period at a predefined time after said programming of said timer.

10. An implantable medical device as claimed in claim 1 wherein said signal detector is a magnetic sensor responsive to an external magnetic field as said external activation.

11. An implantable medical device as claimed in claim 1 wherein said signal detector is an optical sensor responsive to light as said external activation.

12. An implantable medical device as claimed in claim 1 wherein said signal detector is a radio signal detector responsive to radio signals generated by an external programmer that is also used to program said timer.

13. An implantable medical device as claimed in claim 12 wherein said signal detector is responsive to a signaling message comprised of electromagnetic pulses coded to indicate activation, as said external activation.

14. An implantable medical device as claimed in claim 13 wherein said signal detector emits a detector signal in a detection state beginning with said electromagnetic pulses coded to indicate activation, and ends said time period upon detection of a signaling message comprised of electromagnetic pulses coded to mean deactivation, by ceasing to emit said detector signal in said detection state.

15. An implantable medical device as claimed in claim 1 wherein said device components comprise components adapted to stimulate a heart.

* * * * *